United States Patent
Kenmochi et al.

(10) Patent No.: US 7,727,216 B2
(45) Date of Patent: Jun. 1, 2010

(54) DIAPER FOR ADULTS

(75) Inventors: Yasuhiko Kenmochi, Kagawa-ken (JP);
Akiyoshi Kinoshita, Kagawa-ken (JP);
Natsuko Aoyagi, Kagawa-ken (JP);
Naoto Ohashi, Kagawa-ken (JP);
Makoto Ichikawa, Kagawa-ken (JP)

(73) Assignee: Unicharm Corporation, Ehime (JP)

( * ) Notice: Subject to any disclaimer, the term of this patent is extended or adjusted under 35 U.S.C. 154(b) by 198 days.

(21) Appl. No.: 11/773,367

(22) Filed: Jul. 3, 2007

(65) Prior Publication Data

US 2008/0009820 A1 Jan. 10, 2008

(30) Foreign Application Priority Data

Jul. 5, 2006 (JP) .............................. 2006-186104
Mar. 2, 2007 (JP) .............................. 2007-053192

(51) Int. Cl.
*A61F 13/15* (2006.01)
(52) U.S. Cl. .................. 604/389; 604/391; 604/385.27; 604/385.29; 604/385.3; 604/385.11
(58) Field of Classification Search ................. 604/389, 604/391, 385.27, 385.29, 385.3, 385.11
See application file for complete search history.

(56) References Cited

U.S. PATENT DOCUMENTS

| | | | | |
|---|---|---|---|---|
| 2,705,498 A | * | 4/1955 | Johnson | ........................ 604/365 |
| 3,869,761 A | * | 3/1975 | Schaar | ......................... 24/304 |
| 5,342,344 A | * | 8/1994 | Lancaster et al. | ............ 604/387 |
| 6,733,483 B2 | * | 5/2004 | Raufman et al. | ........ 604/385.01 |
| 2002/0099353 A1 | * | 7/2002 | Olson | .......................... 604/389 |
| 2003/0130644 A1 | * | 7/2003 | Baker | .......................... 604/389 |
| 2003/0176846 A1 | * | 9/2003 | Karami | .................. 604/385.29 |
| 2007/0233033 A1 | * | 10/2007 | Ichikawa et al. | ........ 604/385.11 |
| 2007/0250029 A1 | * | 10/2007 | Popp et al. | ............. 604/385.13 |
| 2008/0009816 A1 | * | 1/2008 | Kenmochi et al. | ..... 604/385.01 |
| 2008/0016659 A1 | * | 1/2008 | Peterson | ..................... 24/599.1 |
| 2008/0021431 A1 | * | 1/2008 | Kenmochi et al. | ..... 604/385.23 |

FOREIGN PATENT DOCUMENTS

| | | |
|---|---|---|
| JP | 8-280739 | 10/1996 |
| JP | 2003-70833 A | 3/2003 |
| JP | 2003-88555 A | 3/2003 |
| JP | 2003070833 | * 3/2003 |
| JP | 2006-150068 A | 6/2006 |

* cited by examiner

*Primary Examiner*—Tatyana Zalukaeva
*Assistant Examiner*—Ginger T Chapman
(74) *Attorney, Agent, or Firm*—Brinks Hofer Gilson & Lione

(57) ABSTRACT

A diaper for adults includes a front waist region, a rear waist region and a crotch region extending therebetween, wherein side edge portions of the front and rear waist regions are detachably connected to each other so as to form a waist hole and a pair of leg holes, the side edge portions have a dimension of at least 150 mm as measured in a longitudinal direction, and a position correcting system to correct relative position of first and second fastening components when the first and second waist regions are connected to each other comprises at least one spacing zone defined between setting zones for tow or more fastening components into which the first fastening component is divided in the longitudinal direction.

7 Claims, 5 Drawing Sheets

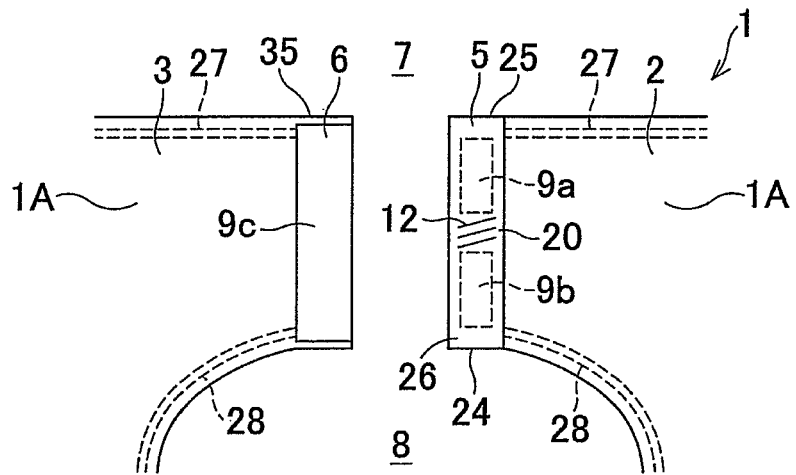
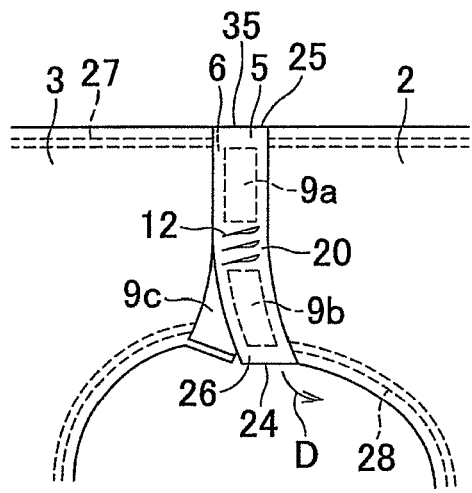
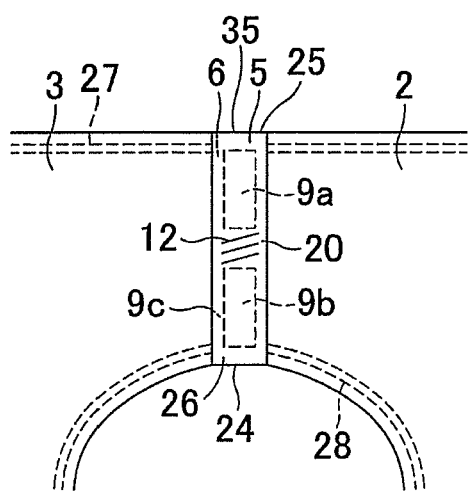

DIAPER FOR ADULTS

BACKGROUND OF THE INVENTION

The present invention generally relates to a diaper for adults.

In recent years, diapers for adults have been in brisk demand. When such diapers for adults are to be put on a wearer who is confined to bed, it has often been the case to use a diaper of pants-type adapted to be opened along transversely opposite lateral margins and to be reclosable along these lateral edges, for example, as disclosed in National Publication of Japanese Translated Version No. 2002-532147 (hereinafter referred to as "Reference").

The diaper disclosed in Reference includes a side panel extending transversely outward from an absorbent assembly in one of waist regions and a mechanical fastening component provided on the other waist region. The side panel is detachably and refastenably engaged with the associated mechanical fastening components from the inside so as to maintain the diaper in the pants-type.

In the case of the diaper disclosed in Reference, the opposite waist regions are refastenably connected together by means of the mechanical fastening component so as to maintain the diaper in the pants-type. However, the diaper disclosed in Reference relates to training pants for baby and necessarily has a size smaller than the diaper for adults. Accordingly, the technique disclosed in Reference can not be directly applied to the diaper for adults without causing various problems.

One of these problems lies in difficulty encountered by the user when the user tries to connect a waist region to the other waist region. While FIG. 2 of Reference illustrates vertically long fastening components, such vertically long fastening components will be too long to be properly engaged one with another over full length thereof in a single procedure. This may result in that the fastening components are not precisely put flat together and, for example, in the case of the mechanical fastener, a surface having a plurality of hooks may be exposed. The hooks exposed in this manner may irritate the wearer's skin, causing the wearer to experience a feeling of discomfort and/or may be caught by the wearer's garment, causing the mechanical fastener to be peeled off from the diaper. Particularly in the case of a surface fastener, the hook carrying sheet usually has a relatively high stiffness and skin irritation due thereto is correspondingly significant. Furthermore, if the hook carrying sheet and the loop carrying sheet are not precisely put flat together, it must be tried again to connect the waist regions to each other after the hook carrying sheet has been peeled off from the loop carrying sheet.

SUMMARY OF THE INVENTION

In view of the problems as have been described above, it is an object of the present invention to provide a diaper for adults improved so that front and rear waist regions can be easily and reliably connected together.

According to the present invention, there is provided a diaper for adults comprising: a longitudinal direction and a transverse direction; a body side surface and a garment side surface; a chassis including a first waist region having an elasticized waist hole defining edge which is one of front and rear waist regions, a second waist region having an elasticized waist hole defining edge which is the other of the front and rear waist regions and a crotch region having elasticized leg hole defining edges and extending between the front and rear waist regions; and a fastening system for detachably connecting transversely opposite side edge portions of the front and rear waist regions to each other. The fastening system comprises a first fastening component extending in the longitudinal direction along the transversely opposite side edge portions of the first waist region, and a second fastening component extending in the longitudinal direction along the transversely opposite side edge portions of the second waist region and being detachably engageable with the first fastening component.

The present invention further comprises a dimension of the transversely opposite side edge portions of the first and second waist regions as measured in the longitudinal direction being at least 150 mm; the transversely opposite side edge portions of at least the first waist region of the first and second waist regions comprising a position correcting system to correct relative position of the first and second fastening components when the first and second waist regions are connected to each other, the position correcting system comprising at least one spacing zone defined between setting zones for two or more fastening components into which the first fastening component is divided in the longitudinal direction, and a tensile strength of at least the spacing zone in the longitudinal direction being lower than that of each of the setting zones.

The present invention may include the following preferred embodiments.

An embodiment wherein the auxiliary position correcting system to correct relative position of the first and second fastening components when the transversely opposite side edge portions of the first and second waist regions are connected to each other is provided in the at least one spacing zone.

An embodiment wherein the auxiliary position correcting system to correct relative position of the first and second fastening components when the transversely opposite side edge portions of the first and second waist regions are connected to each other is provided in a zone of the transversely opposite side edge portions of the second waist region opposite to the at least one spacing zone with transversely opposite side edge portions of the first and second waist regions connected to each other.

An embodiment wherein the auxiliary position correcting system is one of an elastic element extending in the longitudinal direction and at least one silt crossing the spacing zone.

An embodiment wherein the auxiliary position correcting system is an elastic element extending in the longitudinal direction in the zone of the transversely opposite side edge portions of the second waist region opposite to the at least one spacing zone.

An embodiment wherein a dimension of the spacing zone as measured in the longitudinal direction is in a range of 10 mm to 40 mm.

An embodiment wherein a tensile strength at elongation rate of 5% in the spacing zone is lower than a tensile strength at elongation rate of 5% in the setting zone by at least 20 N/25 mm and a tensile strength at elongation rate of 5% in the setting zone is in a range of 25 to 120 N/25 mm.

An embodiment wherein one of the first and second fastening components is a hook element having a plurality of hooks while the other is a loop element having a plurality of loops detachably engageable with the hook element.

According to the present invention, along at least one of the transversely opposite side edge portions of the front and rear waist regions, the fastening components detachably engageable one with another are divided in the longitudinal direction and the position correcting system is provided. With such unique arrangement, it is easily possible to correct relative position of the fastening components by utilizing deformation occurring in a zone of the transversely opposite side edge portions in the waist region between each pair of the adjacent fastening components spaced one from another even if, after one of the two or more fastening components has been engaged, the remaining fastening component(s) is(are) displaced from proper position(s). In this way, an operation of connecting the front and rear waist regions with each other is easily and reliably achieved.

According to the embodiment wherein the auxiliary position correcting system to correct relative position of the fastening components when the front and rear waist regions are connected to each other, it is more easily possible to correct displacement between the fastening components.

BRIEF DESCRIPTION OF THE DRAWINGS

FIG. 2 is a schematic diagram illustrating a manner in which the front and rear waist regions of the diaper according to the first embodiment of the present invention wherein

FIG. 5 is a schematic diagram illustrating a manner in which the front and rear waist regions of the diaper according to the fourth embodiment of the present invention wherein FIG. 5A through FIG. 5C respectively illustrate the similar states to FIG. 2A through FIG. 2C.

DETAILED DESCRIPTION OF THE PREFERRED EMBODIMENTS

Details of a diaper for adults according to the present invention will be more fully understood from the description given hereunder with reference to the accompanying drawings.

First Embodiment

Figure 1:
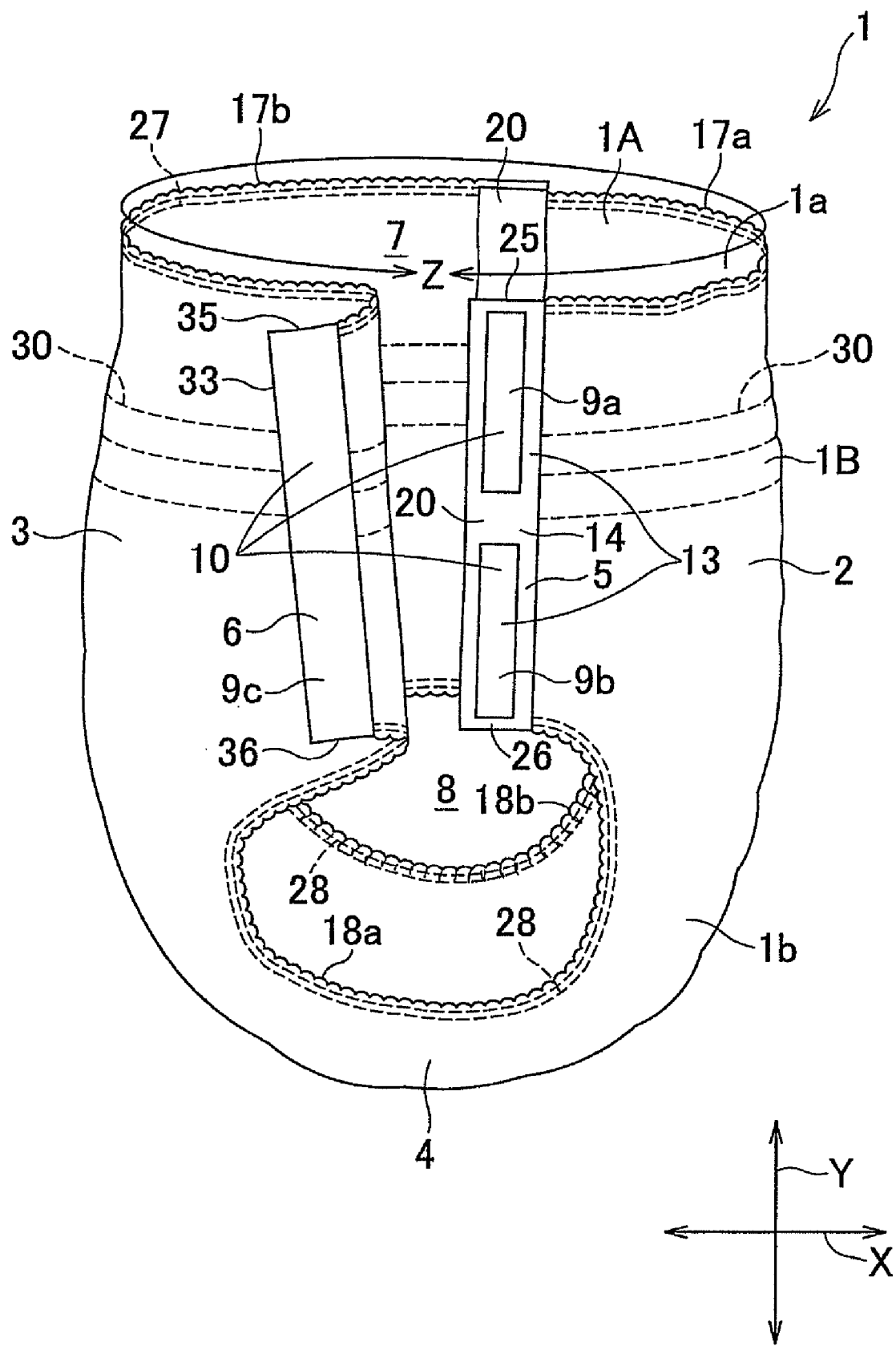
FIG. 1 is a perspective view of a diaper in which one side of side edge portions of front and rear waist regions are disconnected.

In FIG. 1, a diaper comprising a chassis 1 and a fastening system 10 is shown in a perspective view. The chassis 1 comprises a longitudinal direction Y, a transverse direction X and a waist surrounding direction Z, a liquid-pervious body side liner 1A defining a body side surface 1a, a liquid-impervious outer cover 1B defining a garment side surface 1b and a liquid-absorbent core (not shown) disposed between the liner 1A and the cover 1B, a front waist region 2, a rear waist region 3 and a crotch region 4 extending between these two waist regions 2, 3.

Transversely opposite side edge portions 5 (hereinafter only one side of the side edge portions 5 is described) of the front waist region 2 are provided with supporting sheets 20 elongating in the longitudinal direction Y along the side edge portions 5 substantially over full length thereof in the longitudinal direction Y. Two first fastening components 9a, 9b are attached the supporting sheet 20 so as to be spaced apart from each other.

Transversely opposite side edge portions 6 (hereinafter only one side of the side edge portions 6 is described) of the rear waist region 3 are provided on the body side surface 1a along the side edge portions 6 substantially over full length thereof with a second fastening component 9c elongating in the longitudinal direction Y and detachably engageable with the first fastening components 9a, 9b.

When the diaper is put on the wearer's body, the side edge portions 5, 6 of the front waist region 2 and the rear waist region 3 are detachably connected to each other by means of the first fastening components 9a, 9b and the second fastening component 9c so as to obtain the pants-type diaper as shown in FIG. 1.

Thereupon, the pants-type diaper is formed with a waist hole 7 defined by front and rear waist hole defining edges 17a 17b and a pair of leg holes 8 defining by leg hole defining edges 18a, 18b of the crotch region 4. Preferably each of the respective opposite side edge portions 5, 6 has a dimension of at least of 150 mm as measured in the longitudinal direction Y for adult users.

In the waist hole defining edges 17a, 17b and the leg hole defining edges 18a, 18b, elastic elements 27, 28 are attached in a stretched state along the waist hole defining edges 17a, 17b and leg hole defining edges 18a, 18b for elasticizing. In addition, auxiliary elastic elements 30 extending in a waist surrounding direction Z are attached in a stretched state to a substantially middle portion of the front and rear waist regions 2, 3 for enhancing fitness of the diaper to wearer's body. The elastic elements 27, 28, 30 comprise a plurality of rubber strings and contractile force of these rubber strings ensures desired fitness of the waist hole defining edges 17a, 17b and said middle portion to the wearer's body. The rubber strings may be made of natural rubber or synthetic rubber such as polyurethane rubber. Alternatively, the rubber strings may be replaced by an elasticized nonwoven fabric or plastic sheet.

Portions of the waist hole elastic elements 27, 28, 30 crossing the first and second fastening components 9a, 9b, 9c are preferably treated so that these portions might develop neither elastic extension nor elastic contraction. As such treatment, the portion of the elastic elements may be cut, coated with a hot melt adhesive or chemically treated. These portions may be treated in this manner to ensure that the side edge portions 5, 6 may be kept flat in the vicinity of upper and lower edges 25, 26, 35, 36 thereof and these upper and lower edges 25, 26, 35, 36 can be easily held by wearer's hands to connect the front and rear waist regions 2, 3 with each other. In addition, there is no anxiety that the first and second fastening components 9a, 9b, 9c might get wrinkles and thereby strength of engagement between them might be deteriorated.

The body side liner 1A is made of material which is liquid-pervious and provides comfortable touch while the outer cover 1B is made of material which is liquid-impervious and air-permeable. These materials may be appropriately selected from well known materials such as a nonwoven fabric or perforated film made of thermoplastic resin.

The first fastening components 9a, 9b and the second fastening components 9c constitute together so-called mechanical fastener wherein the first fastening components 9a, 9b have a plurality of hooks and the second fastening members 9c have a plurality of loops. Each set of first fastening components 9a, 9b are attached to the garment surface 1b so as to be outside the diaper. The placement of first fastening components 9a, 9b ensures that the wearer's skin is protected from irritation due to the hooks and thereby to prevent the wearer from experiencing feeling of discomfort.

In the side edge portion 5, a spacing zone by which the first fastening components 9a, 9b in each set are spaced from each other in the longitudinal direction Y extends over a substantially longitudinally middle portion of the supporting sheet 20. The supporting sheet 20 is air-permeable and flexible and formed by a nonwoven fabric made of thermoplastic resin. Alternatively, this supporting sheet 20 may be also formed by a perforated resin film.

Each set of first fastening components 9a, 9b are spaced from each other preferably by a distance of 10 mm to 40 mm. If this distance is less than 10 mm, the presence of the spacing zone between the first fastening components 9a, 9b in each set will not be effective to easily correct the relative position of these fastening components. If the distance exceeds 40 mm, a strength of engagement with the second fastening components 9c will be reduced and a fitness of the diaper to the wearer's body will be correspondingly deteriorated. Each set of the first components 9a, 9b are attached to the supporting sheet 20 inside a peripheral edge of this supporting sheet 20 and a longitudinal dimension of the supporting sheet 20 is almost the same as a dimension of the outer cover 1B in the side edge portion 5 as measured in the longitudinal direction Y. A dimension of the individual first fastening components 9a, 9b as measured in the longitudinal direction Y may be appropriately selected within a range of 20 to 150 mm.

The side edge portion 5 is provided with a position correcting system to correct relative position of the first and second fastening components 9a, 9b, 9c when the front and rear waist regions 2, 3 are corrected to each other by the transversely opposite side edge portions 5, 6 of the front and rear waist regions 2, 3. The position correcting system comprises a spacing zone 14 defined between setting zone 13 for two or more first fastening components 9a, 9b and a tensile strength of the spacing zone 14 in the longitudinal direction Y which is lower than that of the setting zone 13. For the setting zone 13 in which the first fastening components 9a, 9b is attached to the supporting sheet 20 in the side edge portion 5 and the spacing zone 14 defined between the first fastening components 9a, 9b in each set, a tensile strength of the spacing zone 14 at elongation rate 5% is preferably lower than that of the setting zone 13 at elongation rate 5% by 20 N/25 mm while the tensile strength of the setting zone 13 at elongation rate 5% is preferably in a range of 25 to 120 N/25 mm.

The side edge portions 5 are destined to come in contact with the wearer's skin and therefore required to be sufficiently flexible to prevent the side edge portions 5 from undesirably irritating the wearer's skin. However, a nonwoven fabric or resin film used as material for the supporting sheet 20 tends to be deformed in undulation as it is held and pulled with wearer's fingers so long as such material is relatively flexible. Upon undulation in the setting zone 13, the first fastening components 9a, 9b are no more flat and it is troublesome to engage these first fastening components 9a, 9b deformed in undulation with the associated second fastening components 9c.

On the condition that the tensile strength of the setting zones 13 at elongation rate of 5% is 25 N/25 mm or higher, the setting zones 13 will not be readily deformed in undulation even when it is held and pulled with the wearer's fingers. Furthermore, unless the tensile strength of the setting zone 13 at elongation rate of 5% exceeds 120 N/25 mm, the desired flexibility is assured and it is not likely that it might irritate the wearer's skin.

By adjusting the tensile strength of the spacing zone 14 at elongation rate of 5% is lower than the tensile strength of the setting zones 13 by at least 20 N/25 mm, it is ensured that, for example, when the first fastening component 9b is held and pulled to correct the position of this first fastening component 9b, deformation occurs primarily in the spacing zone 14 having a relatively low tensile strength at elongation rate of 5% and the setting zone 13 (allocated for the first fastening component 9b) is substantially kept in a flat state. In this way, the first fastening component 9b can be easily brought into engagement with the second fastening component 9c.

The tensile strength of the setting zone 13 at elongation rate of 5% can be adjusted by appropriately selecting the types of the first fastening components 9a, 9b and the supporting sheet 20 or the method for attachment of the first fastening components 9a, 9b to the supporting sheet 20. The method for attachment the first fastening components 9a, 9b to the supporting sheet 20 may be selected from various methods conventionally employed in this field such as adhesion using a hot melt adhesive and heat sealing technique.

For measurement of the tensile strength at elongation rate of 5%, test pieces each having a width of 25 mm and a length of 150 mm are used. Specifically, such test piece is subjected to a tensile test under conditions as follow: distance between chucks (clamps) of 100 mm; strain rate of 100 mm/min; and grab length of 25 mm. A load at elongation rate of 5% is determined. The test piece for the spacing zone 14 is prepared by cutting the material for the supporting sheet 20 in the above-mentioned size and the test piece for the setting zone 13 allocated for the fastening components is prepared by cutting the supporting sheet 20 together with the fastening components permanently bonded thereto in the above-mentioned size. In any cases, the tensile direction corresponds to the transverse direction X for these sheets to be tested, such as the supporting sheet 20.

The second fastening component 9c is permanently bonded to the body side liner 1A in the side edge portions 6 of the rear waist region 3 so that a plurality of loops are in the inner side of the diaper and dimensioned so as to cover completely the associated first fastening components 9a, 9b. In other words, a dimension of the second fastening components 9c as measured in the longitudinal direction Y is longer than a dimension over which each set of the first fastening components 9a, 9b extends in the longitudinal direction Y and a dimension of the second fastening component 9c as measured in the transverse direction X is larger than a dimension of the set of these first fastening components 9a, 9b as measured in the transverse direction X.

An outer side edge 33 of the respective second fastening component 9c and an outermost edge of the side edge portion 6 of the adjacent rear waist region 3 lie in a line. Such arrangement leads to simplification of a process for making the diaper in comparison with the case in which the second fastening component 9c is attached to the side edge portion 6 so as to be spaced apart from the outermost edges of the side edge portion 6. This is for the reason that, after the second fastening components 9c have been attached to continuous web of nonwoven fabric, the second fastening components 9c may be successively bisected to achieve continuous production of the individual diapers.

Bonding of the body side liner 1A and the outer cover 1B to each other and/or attachment of the various members such as the elastic element 27 may be carried out by use of well known means such as hot melt adhesive and heat sealing technique. The liquid-absorbent core may be of prior art.

Figure 2A:
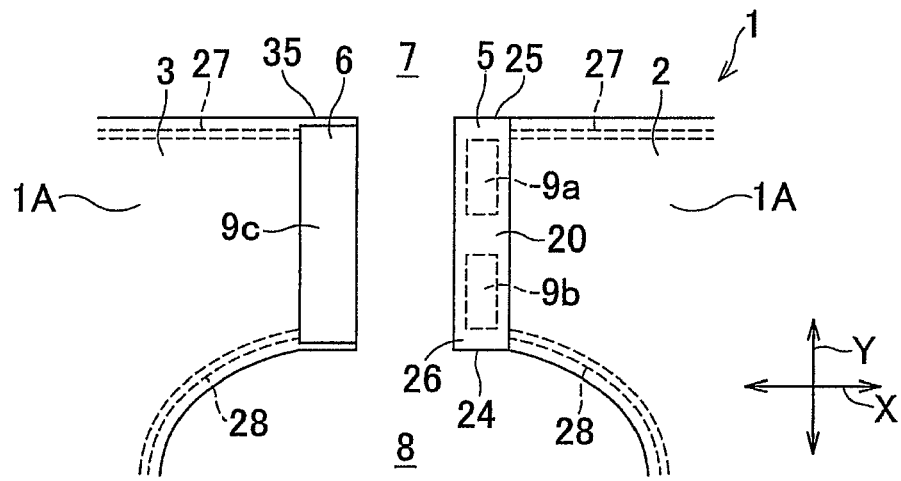
FIG. 2A illustrates the state before the front and rear waist regions are connected together.
Figure 2B:
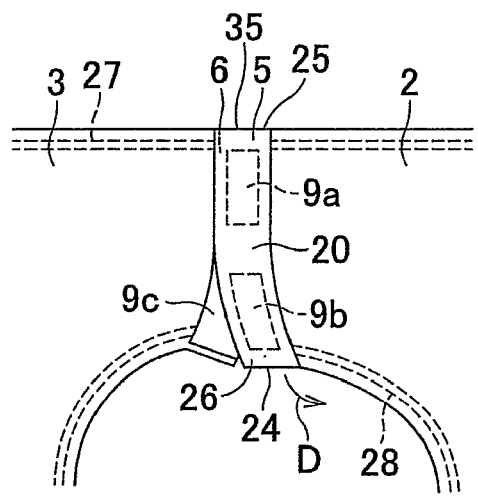
FIG. 2B illustrates the state in the course of the connection and FIG. 2C illustrates the state after the connection has been completed.
Figure 2C:
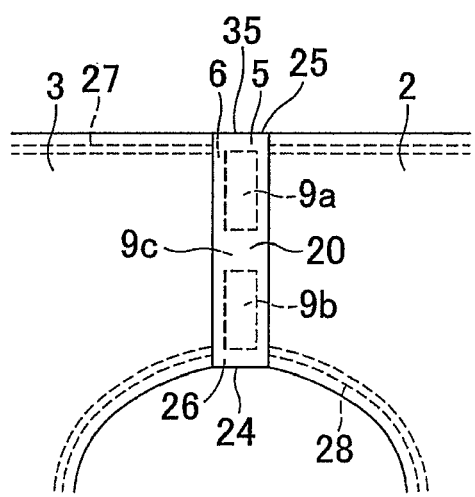

Now a process in which the front and rear waist regions 2, 3 are connected together by means of the first fastening component 9a, 9b and the second fastening components 9c is shown in FIG. 2A through FIG. 2C. FIG. 2A through FIG. 2C are schematic diagrams of the side edge portions 5, 6 on the left side of the wearer as viewed from the inner side of the diaper wherein FIG. 2A illustrates the state before the front and rear waist regions 2, 3 are connected together, FIG. 2B illustrates the state in the course of the connection and FIG. 2C illustrates the state after the connection has been completed.

Starting from the state of FIG. 2A before the front and rear waist regions 2, 3 are connected together, the opposite side edge portions 5, 6 are held with both hands in the vicinity of respective upper edges 25, 26 thereof to place the front and rear waist regions 2, 3 on each other. Then the first fastening component 9a nearer to the upper edge 25 is engaged with the associated second fastening component 9c.

Thereupon, the lower first fastening component 9b is displaced in a direction indicated by an arrow D and partially out of place to overlap with the associated second fastening component 9c under contractile force of the elastic member 28 surrounding the leg hole. Similarly, the second fastening component 9c is also displaced under contractile force of the elastic member 28 surrounding the leg hole. It should be noted here that the side edge portions 5, 6 have a length of at least 150 mm and therefore it is difficult to hold these side edge portions 5, 6 with the single hand during operation of putting the first fastening component 9a into engagement with the associated second fastening component 9c. Consequently, it is impossible to correct said displacement in the course of engaging the first fastening component 9a with the associated second fastening component 9c.

Assumed that the first fastening component 9b has been engaged with the associated second fastening component 9c without correcting the displacement as illustrated in FIG. 2B, the hooks of the first fastening component 9b will be partially exposed on the outer side (the garment side surface 1b) of the diaper and cause troubles, for example, caught by the wearer's clothes. Generally, the fastening component carrying thereon the hooks has a relatively high stiffness and it has usually been difficult to correct the displacement of the first fastening component 9b while the first fastening component 9a remains in engagement with the second fastening component 9c. However, the first fastening components 9a, 9b are spaced apart from each other by at least a distance of 10 to 40 mm and it is not likely that the fastening component 9c might be peeled off from the second fastening component 9c even if the first fastening component 9b alone has been peeled off from the second fastening component 9c. In this way, the fastening component 9b may be refastened to the second fastening component 9c to correct the displacement. Furthermore, the fastening components 9a, 9b are attached on one flexible supporting sheet 20 and therefore the relative position of these first fastening components 9a, 9b can be easily corrected by holding a lower end 24 of the supporting sheet 20 with the fingers and deforming the supporting sheet 20.

That is, according to this embodiment, the portion of the flexible nonwoven fabric material for the supporting member 20 extending between the set of first fastening components 9a, 9b serves as the position correcting system. After completion of engaging the first fastening component 9a with the second fastening component 9c as illustrated in FIG. 2C, displacement of the first fastening component 9b may be corrected and then overlap with the second fastening component 9c. In this way, operation of engagement can be easily performed.

As has been described above, provision of a plurality of the first fastening components 9a, 9b so as to be spaced apart from one another in the longitudinal direction Y improves operability of correction of the front and rear waist regions 2, 3. The arrangement in which the first fastening components 9a, 9b in the same set are spaced apart from each other saves amount of material for the fastening components to be used and correspondingly contributes to cost down.

While the case in which the fastening component 9a is first engaged with the second fastening component 9c has been described above, in case that the fastening component 9b is first engaged with the second fastening component 9c, contractile force of the elastic element 27 surrounding the waist hole causes displacement of the first fastening component 9a. Even in this case, it is possible to correct the displacement of the first fastening component 9a in the manner as has been described above and thereby to overlap the first fastening component 9a with the second fastening component 9c.

Second Embodiment

Referring now to diagrams schematically illustrated in FIG. 3A through FIG. 3C similar to the first embodiment, a second embodiment of the invention will be described. According to this embodiment, a zone of the supporting sheet 20 defined between a set of first fastening components 9a, 9b is provided with an auxiliary position correcting system in form of an elastic element 11 comprising a plurality of rubber strings attached to the supporting sheet 20 in a stretched state so as to extend in the longitudinal direction Y. Under contraction of this elastic element 11, a distance between the first fastening components 9a, 9b in the same set is shorter than in the case of the first embodiment before the diaper is put on the wearer's body. The other aspects are similar to them in the first embodiment and these similar aspects will not be repetitively described.

Figure 3A:
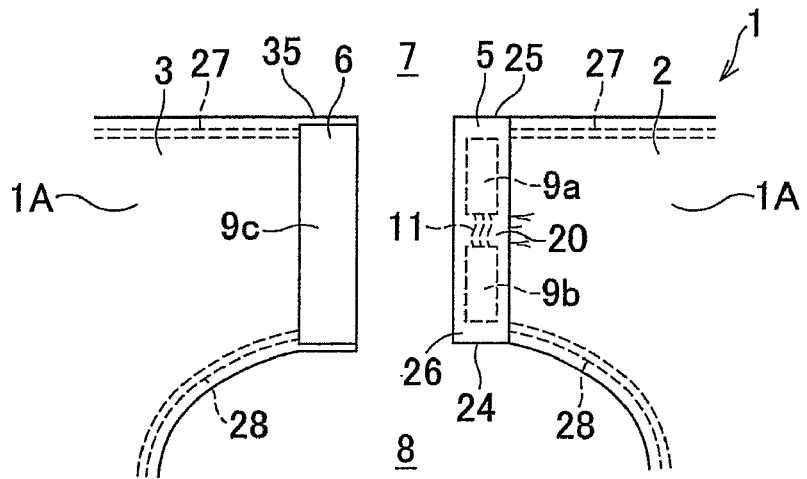
FIG. 3 is a schematic diagram illustrating a manner in which the front and rear waist regions of the diaper according to the second embodiment of the present invention wherein FIG. 3A through FIG. 3C respectively illustrate the similar states to FIG. 2A through FIG. 2C.
Figure 3B:
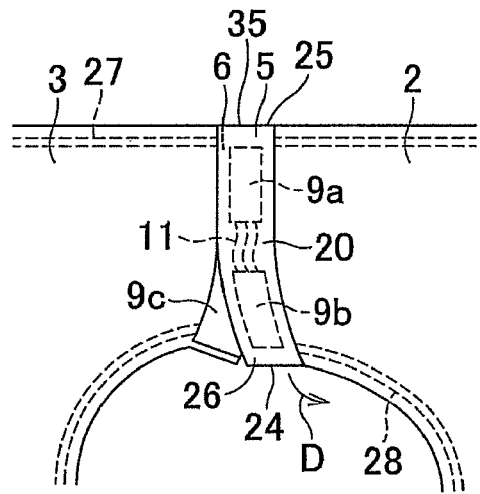
Figure 3C:
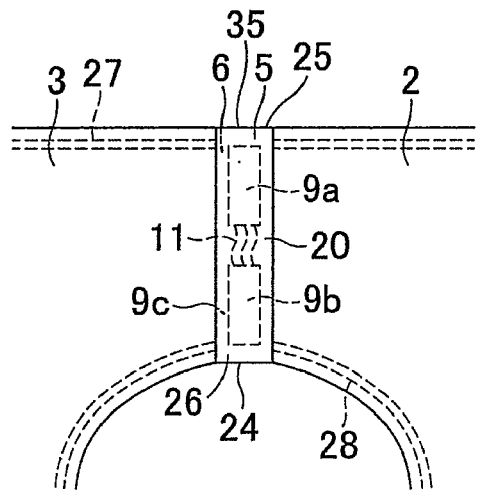

Similarly to the case of the first embodiment, starting from the state of FIG. 3A before the front and rear waist regions 2, 3 are connected together, the opposite side edge portions 5, 6 are held with both hands in the vicinity of respective upper edges 25, 35 thereof. Then the first fastening component 9a nearer to the upper edge 25 is engaged with the associated second fastening component 9c as illustrated in FIG. 3B. Thereupon, the lower first fastening component 9b is displaced in the direction indicated by the arrow D under contractile force of the elastic member 28 surrounding the leg hole.

After the first fastening component 9a has been engaged with the second fastening component 9c, displacement of the first fastening component 9b is overlapped with the second fastening component 9c. In this operation, the lower end 24 of the supporting sheet 20 is held with the fingers and the elastic element 11 extending between the first fastening components 9a, 9b in the same set is kept in a stretched state. By the stretching the elastic element 11 when the first fastening component 9b is overlapped with the second fastening component 9c, it is possible to correct relative position of the first fastening component 9b and the second fastening component 9c in the longitudinal direction Y (i.e., vertical direction as viewed in FIG. 3B) easily.

In other words, correction of relative position of fastening components is facilitated by elastic stretching of the elastic member 11 in the longitudinal direction Y and thereby engaging operation becomes easier. Similarly to the case of the first embodiment, the effect of the present invention is obtained also when the first fastening component 9b is first engaged with the second fastening component 9c.

Third Embodiment

Referring now to diagrams schematically illustrated in FIG. 4A through FIG. 4C similar to the first embodiment, a third embodiment will be described. This embodiment is distinguished from the second embodiment in that the elastic elements 11 serving as the auxiliary position correcting system are provided not on the side edge portion 5 of the front waist region 2 but on the side edge portion 6 of the rear waist region 3.

Figure 4A:
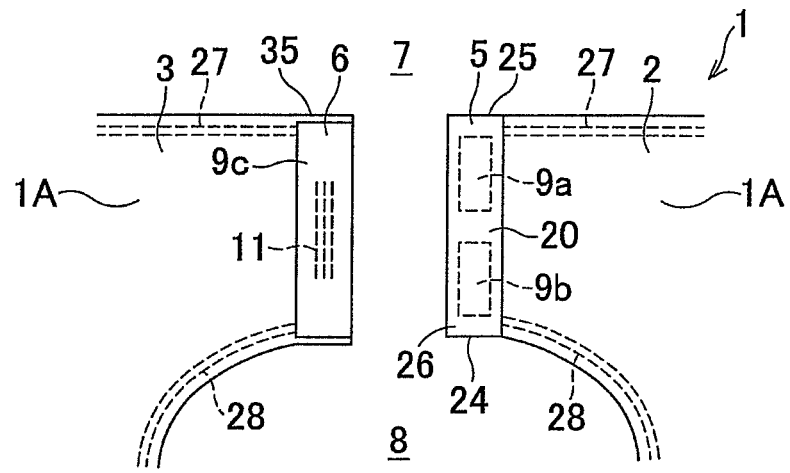
FIG. 4 is a schematic diagram illustrating a manner in which the front and rear waist regions of the diaper according to the third embodiment of the present invention wherein FIG. 4A through FIG. 4C respectively illustrate the similar states to FIG. 2A through FIG. 2C.
Figure 4B:
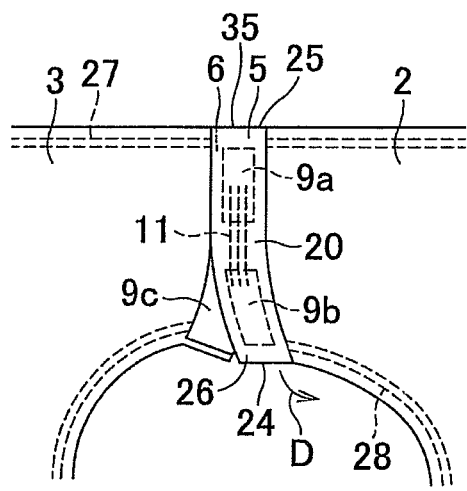
Figure 4C:
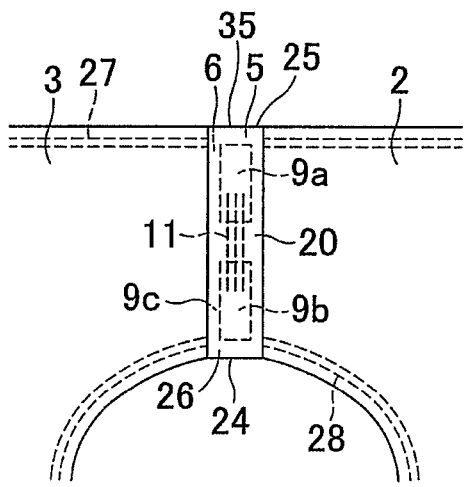

As seen in FIG. 4A, the side edge portion 5 (i.e., the supporting sheet 20) of the front waist region 2 has the first fastening components 9a, 9b attached thereto so as to be spaced apart from each other. The side edge portion 6 of the rear waist region 3 has the second fastening component 9c, but there is only one second fastening component 9c. The second fastening component 9c is provided in a substantially longitudinally middle portion of the second fastening component 9c with the elastic element 11 comprising a plurality of rubber strings. Remaining aspects are similar to those in the second embodiment and will not be repetitively described herein.

Starting from the state of FIG. 4A before connecting operation, the opposite side edge portions 5, 6 are held with both hands in the vicinity of respective upper edges 25, 35 thereof. Then the first fastening component 9a nearer to the upper edge 25 is engaged with the associated second fastening component 9c as illustrated in FIG. 4B. Thereupon, the first fastening component 9b is displaced in the direction indicated by the arrow D under contractile force of the elastic element 28 surrounding the leg hole.

After the first fastening component 9a has been engaged with the second fastening component 9c, displacement of the first fastening component 9b is corrected and then the first fastening component 9b is overlapped with the second fastening component 9c. In this operation, elastic stretching of the elastic element 11 in the longitudinal direction facilitates engaging operation.

Fourth Embodiment

Referring now to diagrams schematically illustrated in FIG. 5A through FIG. 5C similar to the first embodiment, a fourth embodiment will be described. This embodiment is similar to the first embodiment except for that a zone of the supporting sheet 20 defined between the first fastening components 9a, 9b includes a plurality of slits 12 extending obliquely on the side edge portion 5 of the front waist region 2 serving as the auxiliary position correcting system. Remaining aspects are similar to those in the diaper according to the first embodiment and will not be repetitively described herein.

Similarly to the case of the first embodiment, starting from the state of FIG. 5A before connecting operation, the opposite side edge portions 5, 6 are held with both hands in the vicinity of respective upper edges 25, 26 thereof and then the first fastening component 9a nearer to the upper edge 25 is engaged with the associated second fastening component 9c. Thereupon, the lower first fastening component 9b is displaced in a direction indicated by an arrow D under contractile force of the elastic element 28 surrounding the leg hole.

After the first fastening component 9a has been engaged with the second fastening component 9c, displacement of the first fastening 9b is corrected and then the first fastening component 9b is overlapped with the second fastening component 9c. In this operation, the zone of the supporting sheet 20 extending between the first fastening components 9a, 9b in which a plurality of slits 12 are formed further facilitates engaging operation. This is for the reason that the zone tends to be deformed due to widening, elongation and flexion on the slits 12 flexibility of the zone is higher than that in the case of the first embodiment.

It should be understood that the number of the slits 12 as well as the length of the respective slits 12 is not specified. The direction of these slits 12 is preferably out of the machine direction in the step of making the supporting sheet 20 because a nonwoven fabric or plastic film used for the supporting sheet 20 is apt to split off along the machine direction. Similarly to the case of the first embodiment, the effect of the present invention is obtained also when the first fastening component 9b is first engaged with the second fastening component 9c.

While the invention has been described on the basis of several particular embodiments, description of these embodiments is not intended to limit the invention. For example, the first fastening components 9a, 9b on the garment side surface 1b may be replacing the first fastening components 9a, 9b on the body side surface 1a. It is also possible to bisect both the first fastening components 9a, 9b and the second fastening component 9c.

It is possible to dispose the supporting sheets 20 in the side edge portions 6 of the rear waist region 3 or the opposite side edge portions 5, 6 of the front and rear waist region 2, 3 rather than in the side edge portions 5. Furthermore, the supporting sheet 20 may consists of a plurality of divided sheet members rather than a single sheet member. In this case, the setting zones 13 may be formed by separate sheets from the spacing zone 14 and the tensile strength of the spacing zone 14 at elongation rate 5% may be lower than the tensile strength of the setting zones 13 at elongation rate 5% by at least 20 N/25 mm.

Alternatively, the first and second fastening components as the mechanical fastener may be replaced by adhesive fastening members comprising repetitively usable pressure-sensitive adhesive tape and a tape strip adapted to be releasably attached to the adhesive tape. It is also possible to replace the loop element of the mechanical fastener by a nonwoven fabric adapted to be detachably engaged with the hook element. Furthermore, the fastening components may be directly attached to the outer cover 1B without use of the supporting sheet 20.

The entire discloses of Japanese Patent Application Nos. 2006-186104 filed on Jul. 5, 2006 and 2007-53192 filed on Mar. 2, 2007, respectively, including specification, drawings and abstract are herein incorporated by reference in their entirety.

What is claimed is:

1. A diaper for adults comprising:
a longitudinal direction and a transverse direction;
a body side surface and a garment side surface;
a chassis including a first waist region having an elasticized waist hole defining edge which is one of front and rear waist regions, a second waist region having an elasticized waist hole defining edge which is the other of said front and rear waist regions and a crotch region having elasticized leg hole defining edges and extending between said front and rear waist regions;
a fastening system for detachably connecting transversely opposite side edge portions of said front and rear waist regions to each other;
said fastening system comprising a first fastening component extending in said longitudinal direction along said transversely opposite side edge portions of said first waist region, and a second fastening component extending in said longitudinal direction along said transversely opposite side edge portions of said second waist region and being detachably engageable with said first fastening component;

a dimension of said transversely opposite side edge portions of said first and second waist regions as measured in said longitudinal direction being at least 150 nun;

said transversely opposite side edge portions of said first waist region comprising a position correcting system to correct relative position of said first and second fastening components when said first and second waist regions are connected to each other, said position correcting system comprising at least one spacing zone defined between setting zones for two or more fastening components into which said first fastening component is divided in said longitudinal direction, and a tensile strength of at least said spacing zone in the longitudinal direction being lower than that of each of said setting zones; and said transversely opposite side edge portions of said first waist region comprising an auxiliary position correcting system to correct a relative position of said first and second fastening components when said transversely opposite side edge portions of said first and second waist regions are connected to each other, said auxiliary position correcting system comprising an elastic element extending in said longitudinal direction in said at least one spacing zone.

2. The diaper for adults defined by claim 1, wherein a dimension of said spacing zone as measured in said longitudinal direction is in a range of 10 mm to 40 mm.

3. The diaper for adults defined by claim 1, wherein a tensile strength at elongation rate of 5% in said spacing zone is lower than a tensile strength at elongation rate of 5% in said setting zone by at least 20 N/25 mm and a tensile strength at elongation rate of 5% in said setting zone is in a range of 25 to 120 N/25 mm.

4. The diaper for adults defined by claim 1, wherein one of said first and second fastening components is a hook element having a plurality of hooks while the other is a loop element having a plurality of loops detachably engageable with said hook element.

5. A diaper for adults comprising: a longitudinal direction and a transverse direction; a body side surface and a garment side surface;
a chassis including a first waist region having an elasticized waist hole defining edge which is one of front and rear waist regions, a second waist region having an elasticized waist hole defining edge which is the other of said front and rear waist regions and a crotch region having elasticized leg hole defining edges and extending between said front and rear waist regions;
a fastening system for detachably connecting transversely opposite side edge portions of said front and rear waist regions to each other,
said fastening system comprising a first fastening component extending in said longitudinal direction along said transversely opposite side edge portions of said first waist region, and a second fastening component extending in said longitudinal, direction along said transversely opposite side edge portions of said second waist region and being detachably engageable with said first fastening component;
a dimension of said transversely opposite side edge portions of said first and second waist regions as measured in said longitudinal direction being at least 150 mm;
said transversely opposite side edge portions of said first waist region comprising a position correcting system, to correct relative position of said first and, second fastening components when said first and second waist regions are connected to each other, said position correcting system comprising at least one spacing zone defined between setting zones for two or more fastening components into which said first fastening component is divided in said longitudinal direction, and a tensile-strength of at least said spacing zone in the longitudinal direction being lower than that of each of said setting zones; and said transversely opposite side edge portion of said second waist region comprising an auxiliary position correcting system to correct relative position of said first and second fastening components when said transversely opposite side edge portions of said first and second waist regions are connected to each other, said auxiliary position correcting system comprising an
elastic element extending in said longitudinal direction in said second fastening components in said transversely opposite side edge portions of said second waist region opposite to said at least one spacing zone.

6. The diaper for adults defined by claim 5, wherein said elastic element is provided in a substantially longitudinally middle portion of said second fastening component.

7. A diaper for adults comprising:
a longitudinal direction and a transverse direction;
a body side surface and a garment side surface;
a chassis including a first waist region having an elasticized waist hole defining edge which is one of front and rear waist regions, a second waist region having an elasticized waist hole defining edge which is the other of said front and rear waist regions and a crotch region having elasticized leg hole defining edges and extending between said front and rear waist regions;
a fastening system for detachably connecting transversely opposite side edge portions of said front and rear waist regions to each other;
said fastening system comprising a first fastening component extending in said longitudinal direction along said transversely opposite side edge portions of said first waist region, and a second fastening component extending in said longitudinal direction along said transversely opposite side edge portions of said second waist region and being detachably engageable with said first fastening component;
a dimension of said transversely opposite side edge portions of said first and second waist regions as measured in said longitudinal direction being at least 1S0 mm;
said transversely opposite side edge portions of said first waist region comprising a position correcting system to correct relative position of said first and second fastening components when said first and second waist regions are connected to each other, said position correcting system comprising at least one spacing zone defined between setting zones for two or more fastening components into which said first fastening component is divided in said longitudinal direction, and a tensile strength of at least said spacing zone in the longitudinal direction being lower than that of each of said setting zones; and
said transversely opposite side edge portions of said first waist region comprising an auxiliary position correcting system to correct relative position of said first and second fastening components when said transversely opposite side edge portions of said first and second waist regions are connected to each other, said auxiliary position correcting system comprising at least one slit crossing said at least one spacing zone.

* * * * *

UNITED STATES PATENT AND TRADEMARK OFFICE
CERTIFICATE OF CORRECTION

PATENT NO. : 7,727,216 B2
APPLICATION NO. : 11/773367
DATED : June 1, 2010
INVENTOR(S) : Yasuhiko Kenmochi et al.

It is certified that error appears in the above-identified patent and that said Letters Patent is hereby corrected as shown below:

Claim 7, column 12, line 45, delete "1S0 mm;" and substitute "150 mm;" in its place.

Signed and Sealed this

Twenty-sixth Day of October, 2010

David J. Kappos
*Director of the United States Patent and Trademark Office*